United States Patent [19]
Birtwistle et al.

[11] Patent Number: 5,776,444
[45] Date of Patent: Jul. 7, 1998

[54] HAIR TREATMENT COMPOSITIONS

[75] Inventors: David Howard Birtwistle, Bangkok, Thailand; Andrew Malcolm Murray, Parkgate, United Kingdom

[73] Assignee: Chesebrough-Pond's USA Co., Division of Conopco, Inc.

[21] Appl. No.: 628,825

[22] Filed: Apr. 5, 1996

[30] Foreign Application Priority Data

Apr. 6, 1995 [GB] United Kingdom ............... 9507130

[51] Int. Cl.$^6$ .................. A61K 7/07; A61K 7/00
[52] U.S. Cl. ............... 424/70.12; 424/70.11; 424/78.03
[58] Field of Search .............. 424/70.12, 70.11, 424/78.03

[56] References Cited

U.S. PATENT DOCUMENTS

| | | |
|---|---|---|
| 2,891,920 | 6/1959 | Hyde et al. . |
| 3,294,725 | 12/1966 | Findlay et al. . |
| 3,360,491 | 12/1967 | Axon . |
| 4,902,499 | 2/1990 | Bolish, Jr. et al. . |
| 4,906,459 | 3/1990 | Cobb ............................ 424/70 |
| 5,354,564 | 10/1994 | Borish .......................... 424/490 |
| 5,523,081 | 6/1996 | Edwards ....................... 424/73 |
| 5,554,313 | 9/1996 | Chandler ...................... 510/121 |

FOREIGN PATENT DOCUMENTS

| | | |
|---|---|---|
| 0 240 350 | 10/1987 | European Pat. Off. . |
| 0 268 982 | 6/1988 | European Pat. Off. . |
| 0 381 318 | 2/1989 | European Pat. Off. . |
| 0 445 982 | 9/1991 | European Pat. Off. . |
| 0 468 721 | 1/1992 | European Pat. Off. . |
| 0 529 883 | 3/1993 | European Pat. Off. . |
| WO 91/16878 | 11/1991 | WIPO . |
| WO 95/09599 | 4/1995 | WIPO . |

*Primary Examiner*—Sally Gardner-Lane
*Attorney, Agent, or Firm*—Milton L. Honig

[57] ABSTRACT

Hair treatment compositions which can generate style benefits while giving good conditioning comprise a non-rigid, emulsion polymerised cross-linked silicone conditioning polymer having from about 0.05% to about 10% branched monomer units.

10 Claims, No Drawings

HAIR TREATMENT COMPOSITIONS

FIELD OF INVENTION

The invention relates to hair treatment compositions containing particular types of silicones which can generate style benefits while giving good conditioning.

BACKGROUND OF INVENTION AND PRIOR ART

The use of silicones as conditioning agents in hair treatment compositions is well known and widely documented in the patent literature. However, a problem associated with such materials is that their use at levels necessary for achieving good tactile and/or visual benefits can make the hair too soft to style or retain a style. Fine hair in particular can appear limp and unmanageable.

Accordingly, stylability is generally achieved by application of film-forming materials to the hair, usually after shampooing and/or conditioning, in the form of mousses, gels or sprays. However, the adhesive and/or resinous materials used frequently for style retention can damage dry hair properties, especially hair feel and ease of dry combing. Also, many people require a degree of stylability improvement without the inconvenience and cost of a separate step.

Highly viscous silicones have the ability to modify the condition and manageability of hair. Siloxane gums improve the combability, softness and condition of the hair and reduce its susceptibility to damage due to mechanical manipulation caused for example by brushing and styling. Silicone resins give body to fine, limp hair and increase the ability of hair to hold a style.

EP-A-240 350 and U.S. Pat. No. 4,902,499 (Procter & Gamble) for example disclose the use of specific rigid silicone polymers dissolved in a volatile carrier material for giving improved style retention to hair. The polymers described are incorporated in the form-of an aqueous silicone emulsion comprising an anionically stabilised hydroxylated polyorganosiloxane, colloidal silica and a catalyst, which crosslinks to form an elastomer on the hair when the water content dries out. Also mentioned are siloxanes, which are required to be soluble in solvents such as cyclomethicone.

EP-A-0 468 721 (Unilever) describes how highly viscous silicones are extremely difficult to incorporate into a shampoo product because they cannot themselves be dispersed to form droplets or an emulsion and must first be dissolved in a volatile solvent, such as a volatile silicone.

The need to use solvents or carriers is disadvantageous for several reasons. For example, products obtained through the use of such solvents or carriers are prone to significant thinning, thereby making it necessary to use a thickening agent to provide a product of commercially and aesthetically acceptable viscosity. Furthermore, volatile organic solvents or carriers generally act as foam suppressors and therefore impair the foamability and ease of spreading of products, especially shampoos, containing them. They can also affect the conditioning properties of the silicone and their volatility can cause safety hazards during processing.

EP-A-0445982 (Dow Corning) discloses the use for hair conditioning purposes of emulsion polymerised highly branched and crosslinked polydimethylsiloxane (including less than about 40% of linear silicone polymer) in a hydrophobic cationic emulsion. EP-A-0381318 (Dow Corning) discloses hair conditioning compositions comprising certain polydiorganosiloxane-polyoxalkylene copolymers, not in the form of emulsion polymers.

Our copending application PCT/EP94/03233 (WO95/09599) describes hair conditioning shampoo compositions containing non-volatile insoluble dimethiconol nonionic conditioning polymer which is emulsion polymerised, thereby obviating the need for an organic solvent for the gum. The specification refers in passing to the possibility of the dimethiconol polymer being cross-linked but there is no discussion and no examples of this and no appreciation of the styling benefits of cross-linking. Emulsion polymerised silicones as such are known from U.S. Pat. No. 2,891,920 (Hyde), U.S. Pat. No. 3,294,725 (Findlay) and U.S. Pat. No. 3,360,491 (Axon).

We have now found that emulsion polymerised silicones which are cross-linked in the emulsion form give improved styling benefits without compromising conditioning properties when formulated into a hair treatment composition. Cross-linking in emulsion form gives more precise control of the level of cross-linked silicone deposited on the hair compared with systems which cross-link during drying onto the hair, and greater ease of formulation compared with systems which employ an organic solvent or carrier of the silicone.

DEFINITION OF THE INVENTION

The present invention provides a hair treatment composition comprising a non-rigid emulsion polymerised cross-linked silicone conditioning polymer, in which the polymer has from about 0.05% to about 10% branched monomer units.

DETAILED DESCRIPTION OF THE INVENTION

The non-rigid emulsion-polymerised cross-linked silicone conditioning polymer is preferably present in compositions of the invention in an amount from about 0.01% to about 50% by weight based on the total weight of the composition, more preferably from about 0.1 to about 20% by weight, most preferably from about 0.3 to about 10% by weight.

Preferred silicone conditioning polymers for use in the invention are polydiorganosiloxanes, preferably derived from suitable combinations of $R_3SiO_{0.5}$ units and $R_2SiO$ units where each R independently represents an alkyl, alkenyl (e.g., vinyl), alkaryl, aralkyl, or aryl (e.g. phenyl) group. R is most preferably methyl.

The preferred silicone conditioning polymers of the invention are cross-linked polydimethyl siloxanes (which have the CTFA designation dimethicone), optionally having end groups such as hydroxyl. Good results have been obtained with dimethicone.

Cross linking of the silicone conditioning polymer is typically introduced concurrently during emulsion polymerisation of the polymer through the inclusion of the required amount of trifunctional and tetrafunctional silane monomer units, for example, those of formula R Si (OH)$_3$ wherein R represents an alkyl, alkenyl (e.g. vinyl), alkaryl, aralkyl or aryl (e.g. phenyl) group, preferably methyl.

The degree of cross-linking of the silicone conditioning polymer can be measured as the percentage of branched monomer units in the silicone conditioning polymer and is suitably from about 0.05% to about 10%, preferably being in the range about 0.15 to about 7%, e.g.,from about 0.2% to about 2%. Increasing cross-linking is found to improve styling benefits but also to reduce conditioning performance somewhat, so compromise levels must be selected with properties optimised to suit consumer preferences in different cases. Good overall performance has been obtained with dimethicone 0.6% cross-linked.

Suitable emulsion polymerised cross-linked silicone conditioning polymers are commercially available or can be readily made using conventional techniques well known to those skilled in the art.

Advantageously, the viscosity of the silicone conditioning polymer is at least $10^6$ cst to give good styling benefits and preferably does not exceed $10^9$ for ease of formulation.

Preferably, the average particle size of the silicone material of the silicone conditioning polymer is less than 20 microns, more preferably less than 2 microns. Small particle size enables a more uniform distribution of silicone conditioning polymer on the hair for the same concentration of silicone in the hair treatment composition described. Particle size may be measured by means of a laser light scattering technique, using a 2600D Particle Sizer from Malvern Instruments.

Hair treatment compositions according to the invention may suitably take the form of shampoos, conditioners, sprays, mousses or lotions. Particularly preferred forms are shampoos, conditioners and mousses, including "3-in-1" styling shampoos, having cleaning, conditioning and styling properties.

A preferred hair treatment composition in accordance with the invention is a shampoo composition which, in addition to the silicone conditioning polymer comprises (further) surfactant to provide a deterging benefit. The deterging surfactant is selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 0.1 to 50% by weight, preferably from 0.5 to 30% by weight.

Hair treatment compositions in accordance with the invention may also take the form of hair conditioning compositions, which preferably comprise one or more cationic surfactants. The use of cationic surfactants is especially preferred, because these ingredients are capable of providing conditioning benefits to hair.

Examples of cationic surfactants include:

quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethyammonium hydroxide, hexadecyltrimethylammonium hydroxide, cetyltrimethylammonium hydroxide, octyldimethylbenzylammonium hydroxide, decyldimethylbenzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides Cetylpyridinium hydroxide or salts thereof, e.g., chloride Quaternium –5

Quaternium –31

Quaternium –18 and mixtures thereof.

In hair conditioning compositions according to the invention, the level of cationic surfactant is preferably from 0.01 to 10%, more preferably 0.05 to 5%, most preferably 0.1 to 2% by weight of the composition.

Hair treatment compositions of the invention may also contain one or more additional conditioning agents, preferably selected from cationic polymers, protein hydrolyzates and quaternised protein hydrolysates.

Suitable cationic polymers include:

Guar hydroxypropyltrimmonium chloride

Poly(dimethyldiallyammonium chloride)

Poly(dimethylbutenyl ammonium chloride) -a,w-bis(triethanolammonium chloride)

Poly(dipropyldiallyammonium chloride)

Poly(methyl-B-propaniodiallyammonium chloride)

Poly(diallypiperidinium chloride)

Poly(vinyl pyridinium chloride)

Quaternised poly (vinyl alcohol)

Quaternised poly (dimethylaminoethylmethacylate)

Poly-Quaternium 7

Poly-Quaternium 10

Poly-Quaternium 11

Poly-Quaternium 22

Poly-Quaternium 16 and mixtures thereof.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

A further optional component of hair treatment compositions of the invention is a deposition aid, preferably a cationic deposition polymer.

The cationic deposition aid will generally be present at levels of from 0.001 to 5%, preferably from about 0.01 to 1%, more preferably from about 0.02% to about 0.5% by weight. The polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8.

The cationic nitrogen-containing group will generally be present as a substituent on a fraction of the total monomer units of the cationic deposition polymer. Thus when the polymer is not a homopolymer it can contain spacer non-cationic monomer units. Such polymers are described in the CTFA Cosmetic Ingredient Directory, 3rd edition.

Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

The cationic deposition aids can comprise mixtures of monomer units derived from amine- and/or quaternary ammonium-substituted monomer and/or compatible spacer monomers.

Suitable cationic deposition aids include, for example: copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA", as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gaf Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in our copending UK Application No. 9403156.4 (WO95/22311).

Other cationic deposition aids that can be used include polysaccharide polymers, such as cationic cellulose derivatives and cationic starch derivatives.

Cationic polysaccharide polymer materials suitable for use in compositions of the invention include those of the formula:

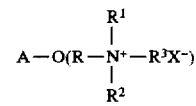

wherein:
A is an anhydroglucose residual group, such as starch or cellulose anhydroglucose residual,
R is an alkylene oxyalklene, polyoxyalkylene, or hydroxyalkylene group, or combination thereof,
$R^1$, $R^2$ and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion as previously described.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

As discussed above, the cationic deposition aid is water soluble. This does not mean, however, that it must be soluble in the hair treatment composition. Preferably, however, the polymer is either soluble in the composition, or in a complex coacervate phase in the composition, formed by the polymer and anionic material. Complex coacervates of the polymer can be formed with anionic surfactants or with anionic polymers that can optionally be added to the compositions of the invention (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature.

It is believed to be particularly advantageous for the cationic deposition aid to be present in the composition in a coacervate phase, or to form a coacervate phase upon application or rinsing of the composition to or from the hair. Complex coacervates are believed to more readily deposit on the hair. Thus, in general, it is preferred that the deposition aid exist in the composition as a coacervate phase or form a coacervate phase upon dilution. If not already a coacervate in the composition, the deposition aid will preferably exist in a complex coacervate form in the composition upon dilution with water to a water: composition weight ratio of about 20:1, more preferably at about 10:1, even more preferably at about 8:1.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

Preferably the deposition aid is selected from the group comprising cationic polyacrylamides, hydroxyalkyl cellulose ethers and cationic guar derivatives. Particularly preferred deposition aids are Jaguar C13S with a cationic charge density of 0.8 meq/g. Jaguar C13S is guar hydroxypropyltriamonium chloride. Other particularly suitable materials include Jaguar C15, Jaguar C17 and Jaguar C16 and Jaguar C162. A preferred cellulose ether is Polymer JR400.

The composition may further comprise from 0.1 to 5 % of a silicone suspending agent selected from selected from polyacrylic acids cross linked polymers of acrylic acid, copolymers of acrylic acid with a hydrophobic monomer, copolymers of carboxylic acid- containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and Polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark.

Suitable cross linked polymers of acrylic acid and acrylate esters are Pemulen TR1 or Pemulen TR2. A suitable heteropolysaccharide gum is xanthan gum, for example that available as Kelzan mu.

Another ingredient that may advantageously be incorporated into hair treatment compositions of the invention is a fatty alcohol material. The use of such materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invent ion.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

Hair treatment compositions in accordance with the invention may also take the form of aerosol foams (mousses) in which case a propellant must be included in the composition. This agent is responsible for expelling the other materials from the container and forming the hair mousse character.

The propellant gas can be any liquefiable gas conventionally used for aerosol containers. Examples of suitable propellants include dimethyl ether, propane, n-butane and isobutane, used singly or in admixture.

The amount of the propellant gases is governed by normal factors well known in the aerosol art. For hair mousses, the level of propellant is generally from about 3% to about 30%, preferably from about 5% to about 15% of the total composition.

Small quantities of surfactant ranging anywhere from 0.1 to about 10%, preferably from about 0.1 to about 1%, most preferably about 0.3% by weight may be present in the hair mousse compositions of the invention. The surfactant may be an anionic, nonionic or cationic emulsifier. Particularly preferred are nonionic emulsifiers which are formed from alkoxylation of hydrophobes such as fatty alcohols, fatty acids and phenols.

Depending on the type of composition employed, one or more additional ingredients conventionally incorporated into hair treatment compositions may be included in compositions of the invention. Such additional ingredients include styling agents, such as resins and hair-setting polymers, perfumes, dyes, buffering or pH adjusting agents, viscosity modifiers, opacifiers, pearlescers, preservatives, antibacterial agents, antidandruff agents, foam boosters, proteins, moisturising agents, herb or other plant extracts and other natural ingredients.

The invention is further illustrated by way of the following non-limitative examples:

EXAMPLE 1

A shampoo composition was prepared by mixing the following components in the amounts stated.

| Component | % by weight |
| --- | --- |
| Sodium lauryl ether sulphate 2EO | 16.0 |
| Cocamidopropyl betaine | 2.0 |
| Jaguar C13S | 0.2 |
| CARBOPOL 980 | 0.4 |
| Silicone[1] | 3.3 |
| Preservative, colour, fragrance | q.s. |
| Water | to 100% |

[1] Emulsion polymerized dimethicone containing 0.6% cross-linking, 60% aqueous emulsion, ex Dow Corning.

The silicone is non-rigid, has a viscosity of $8 \times 10^7$ cps and a particle size of 0.5 microns.

In this and the following Examples, the % of cross-linking of the silicone refers to the % of branched monomer units in the silicone.

EXAMPLE 2

A shampoo composition was prepared by mixing the following components in the amounts stated.

| Component | % by weight |
| --- | --- |
| Sodium lauryl ether sulphate 2EO | 8.0 |
| Cocamidopropyl betaine | 4.0 |
| Jaguar C13S | 0.1 |
| EUPERLAN PK3000[2] | 8.0 |
| Silicone[3] | 3.3 |
| Preservative, colour, fragrance | q.s. |
| Water | to 100% |

[2] Mixture of SLES 4EO, glycol distearate and cocamidopropyl betaine, ex Henkel
[3] Non-rigid emulsion polymerised dimethicone containing 1.8% cross-linking, 60% aqueous emulsion, ex Dow Corning.

The shampoo compositions of Examples 1 and 2 act to clean, condition and style hair. The surfactant (sodum lauryl ether sulphate 2EO) cleans the hair and the cross-linked silicone conditions and styles.

EXAMPLE 3

A hair conditioning composition was prepared by mixing the following components in the amounts stated.

| Component | % by weight |
| --- | --- |
| Cetyl trimethylammonium chloride | 0.7 |
| Cetostearyl alcohol | 1.2 |
| Glyceryl monostearate | 0.7 |
| Paraffin wax | 1.0 |
| Silicone[4] | 3.3 |
| Preservative, colour, fragrance | q.s. |
| Water | to 100% |

[4] As in Example 1

EXAMPLE 4

A hair mousse was prepared by mixing the following components in the amounts stated.

| Component | % by weight |
| --- | --- |
| Silicone[5] | 1.0 |
| EMPILAN NP9[6] | 0.3 |
| Butane/propane | 5.5 |
| Preservative, fragrance | q.s. |
| Water | to 100 |

[5] As in Example 1
[6] Nonyl phenol ethoxylate 9EO, ex Albright & Wilson

The compositions of Examples 1 to 4 gave both styling and conditioning benefits to hair.

The styling and conditioning performance of a shampoo composition with the formulation as in Example 1, and variants including silicones with different percentages of cross-linking, and also a non cross-linked silicone emulsion polymer (referred to as X2-1784) as disclosed in Example 2 of WO95/09599 were tested in the following Examples.

EXAMPLE 5

Measurement of styling in vitro

This test measures the development of curl in hair switches.

a) Switch Preparation

Ten grams of hair was prepared into switches. Six such switches were then layered (removing 2 g hair) and permed around 6×1 cm rollers using a perm kit.

b) Switch Treatment

The switches were split into two groups of three and one group was washed twice for 30 secs with 1 g of shampoo and rinsed for 60 secs. The other group was washed in the same way with another shampoo for comparision. The switches were then scrunched dry with fingers and dried with a hairdryer to generate curls.

c) Evaluation

After styling the switches were ranked by a team of 12 trained panellists for perm drop (the panellists' perception of the total length of the main body of the switch) on a scale of 1 to 6.

The average score for each switch was calculated, then the average score for each treatment was calculated. The total score for the two treatments being compared is always 7, with the maximum split being 5–2. The results are expressed as relative perm drop, i.e. product 1 score–product 2 score. A positive result means that product 1 is better than product 2, with a score of +3.0 (5–2) being the maximum score. Results were as follows.

| Level of cross-linker | Perm Drop (1–2) |
| --- | --- |
| 0.15 v 0.0 | 2.0 |
| 0.6 v 0.0 | 3.0 |
| 0.6 v 0.15 | 3.0 |
| 0.6 v 1.8 | 1.0 |
| 0.6 v 7.0 | −3.0 |
| 0.6 v X2-1784 | 3.0 |

The results show that the cross-linked silicone gives a styling benefit over uncross-linked silicone and also over the X2-1784 non cross-linked conditioning emulsion polymer as described in WO95/09599. The results also show that increasing the percentage of cross-linking improves the styling performance.

EXAMPLE 6

Conditioning performance

The condition of the switches after washing in the shampoos used in Example 5 was measured by dry combing as follows.

7 g of hair in the form of a switch was worked in 0.7 g shampoo, lathered for 30 seconds, and rinsed with water. The procedure was repeated once. Three switches of hair were prepared for each product to be evaluated. The evaluation of dry combing was carried out by twelve trained pannelists as a paired comparison test and significant differences at greater than 95% confidence was assessed. Results are shown in the following table, with each row including entries for two shampoos being compared in the form of relative allocation of a total score of 100, a higher score indicating preference for that member of the pair.

| X2-1784 | 0% XL | 0.15% XL | 0.6% XL | 1.8% XL | 7.0% XL |
|---|---|---|---|---|---|
| 72 | 28* | | | | |
| | 85 | 15* | | | |
| | | 51 | 49 | | |
| | | 76 | | 24* | |
| | | 68 | | | 32* |

*indicates results significantly different at greater than 95% confidence level.

The results show that conditioning deteriorates as cross linking increases; thus there is a trade off between conditioning and styling. The optimum will depend on consumer preference.

EXAMPLE 7

The shampoo of Example 1 (0.6% cross-linked silicone) was compared with a control silicone based conditioning shampoo sold in the UK under the trade name "PANTENE 2 in 1". The compositions were used to treat identical hair switches which were then subjected to a series of paired comparison tests by trained panellists. The two attributes considered to be most indicative of conditioning benefit are (a) ease of dry combing and (b) smooth feel of the hair when dry.

The shampoo of Example 1 was found to be at least as good as the control in both tests.

We claim:

1. A hair treatment composition comprising from about 0.01 to about 50% by weight of a non-rigid, emulsion-polymerised cross-linked silicone conditioning polymer, in which the polymer has from about 0.05% to about 2% branched monomer units.

2. A composition according to claim 1, in which the silicone conditioning polymer is a cross-linked dimethicone.

3. A composition according to claim 1, in which the silicone conditioning polymer has from about 0.15% to about 0.6% branched monomer units.

4. A composition according to claim 1, in which the viscosity of the silicone conditioning polymer lies in the range $10^6$ to $10^9$ cst.

5. A composition according to claim 1 claims, in which the average particle size of the silicone conditioning polymer is less than 20 microns.

6. A composition according to claim 1 claims, which is a hair styling composition.

7. A composition according to claim 1, which is a shampoo comprising from about 0.1 to about 50% by weight of at least one surfactant selected from the group consisting of anionic, nonionic, amphoteric surfactants and mixtures thereof.

8. A composition according to claim 1, which is a conditioning composition containing one or more conditioning agents.

9. A composition according to claim 1, comprising at least one of a deposition aid and a fatty alcohol material.

10. A composition according to claim 9, comprising from about 0.01 to about 5% by weight of a deposition aid which is a cationic polymer selected from the group consisting of hydroxyalkyl cellulose ethers, cationic guars and cationic polyacrylamides.

* * * * *